(12) United States Patent
Smith

(10) Patent No.: US 8,420,131 B2
(45) Date of Patent: *Apr. 16, 2013

(54) COMPOSITION FOR OBESITY TREATMENT

(76) Inventor: Conrad Anton Smith, Sandton (ZA)

( * ) Notice: Subject to any disclaimer, the term of this patent is extended or adjusted under 35 U.S.C. 154(b) by 0 days.

This patent is subject to a terminal disclaimer.

(21) Appl. No.: 13/189,835

(22) Filed: Jul. 25, 2011

(65) Prior Publication Data

US 2013/0028988 A1 Jan. 31, 2013

(51) Int. Cl.
*A01N 65/00* (2009.01)

(52) U.S. Cl.
USPC .......................................................... 424/725

(58) Field of Classification Search .................. None
See application file for complete search history.

(56) References Cited

U.S. PATENT DOCUMENTS

| 7,476,406 | B1 | 1/2009 | Smidt |
| 2005/0249827 | A1 | 11/2005 | Gardiner et al. |
| 2006/0040003 | A1 | 2/2006 | Needleman et al. |
| 2006/0280815 | A1 | 12/2006 | Gardiner et al. |
| 2010/0113494 | A1 | 5/2010 | Hu et al. |

FOREIGN PATENT DOCUMENTS

| EP | 2 070 926 | 6/2009 |
| JP | 2010-202634 | 9/2010 |
| WO | 2005-107779 | 11/2005 |
| WO | 2010/104595 | 9/2010 |

OTHER PUBLICATIONS

International Search Report issued Sep. 3, 2012 in International (PCT) Application No. PCT/ZA2011/000054.

*Primary Examiner* — Michael Meller

(74) *Attorney, Agent, or Firm* — Wenderoth Lind & Ponack, L.L.P

(57) ABSTRACT

This invention relates to a composition of a unique combination of three novel dietary supplements for use in a weight loss program. The composition includes a mood enhancer, an insulin sparing agent, and a peripheral energy blocker. Also provided is a method of treatment in a weight loss program.

5 Claims, No Drawings

COMPOSITION FOR OBESITY TREATMENT

BACKGROUND OF THE INVENTION

This invention relates to the unique combination of three novel dietary supplements for use in a weight loss program.

The worldwide phenomenon of weight gain, despite various attempts at dietary intervention and exercise, indicates that the current mechanisms of regulating energy balance and body weight are not able to cope with obesity-promoting genetic makeup as well as the modern food environment, where calories are abundant and relatively inexpensive.

Moderate weight loss achievements, however, are recognised to have major health benefits for overweight individuals, and increases life-expectancy in those with obesity-related complications. A reduced energy intake combined with increased energy expenditure is known to be an effective weight-loss strategy. Research however has documented that only one third of those trying to lose weight reported eating fewer calories and exercising more. In addition, it has been estimated that 90% of those who lose weight through dieting will return to their original weight within 2-5 years.

This suggests that mono-therapy to reduce body weight cannot cope with the level of over-consumption triggered by modern society. It has therefore been proposed that combination therapies might provide a better future solution.

Rather than the current single-product/single-programme approach to treat obesity, this invention relates to a usage in combination of three novel nutritional agents simultaneously, with each agent targeting a different obesity-promoting category.

Used on their own, each of the three nutritional agents displays a unique weight-loss benefit within its own distinctive category and can effectively be used to treat or prevent obesity as a single or standalone treatment strategy.

This patent application, however, is based on the strategy that the combination of the three agents simultaneously is novel, synergistic and unique, and presents an improvement to prior models. This postulation is supported by original research that demonstrates that the combination of the three products simultaneously, achieves better results, compared to each agent used as a standalone agent during testing.

Numerous mechanisms control appetite, behaviour and energy regulation. For clarification purposes, these factors will be divided into three broad categories, namely: A—behaviour B—metabolism and C—food environment, and will be discussed in this sequence in this specification.

Category A: Behaviour

Most people gain weight because they eat too much. This could merely be because of bad habits, but often over-eating stems from emotional and medical conditions that make appetite control very difficult. The inventor has demonstrated that large numbers of obese individuals had undiagnosed psychological disorders such as the Binge Eating Disorder (Obsessive Compulsive Disorder), Attention Deficit Disorder (ADHD/ADD) and other mood disorders, (such as depression) and anxiety disorders (such as Generalised Anxiety Disorder), conditions that all lower levels of compliance and motivation. Giving these individuals a meal-plan of whatever kind without helping them address their underlying perceptive emotional disorder sets them up for failure right from the start and is therefore a futile exercise.

Successful weight-loss requires sustained effort, fuelled by motivation, which in turn is dependent on many other factors, including mood. Happiness and contentment are not static processes and it is difficult to maintain positive emotions like optimism, self-confidence and emotional tranquillity. Many persons must deal with difficult people on a daily basis, and can become emotionally drained and physically exhausted by numerous responsibilities. A successful solution to this problem has led the inventor to develop a mood stabiliser.

Category B: Metabolism

The phenomenon where some individuals can consume significantly more food calories than others, without gaining weight, is well known. This has been attributed to differences, some genetic and others acquired, which are numerous and complex, but can in many instances be explained on the basis of an acquired medical condition called 'insulin resistance', of which obesity is a major precipitating factor.

The single most important controller of organic metabolism is the hormone insulin, and not the thyroid hormone, as what is often mistakenly stated.

Insulin has several different effects that lead to fat accumulation in adipose tissue. Firstly, insulin promotes fat synthesis. When the quantity of glucose that enters the liver cells is more than what can be stored as glycogen, insulin promotes the conversion of excess glucose into fatty acids. These fatty acids are subsequently packaged as triglycerides in very low density lipoproteins and transported to the adipose tissue where they are deposited as fat. However, insulin also increases the utilisation of glucose by most of the body's tissues, which automatically decreases the utilisation of fat, thus functioning as a "fat sparer".

Secondly, insulin plays a role in fat storage. By inhibiting the action of hormone-sensitive lipase, an enzyme that causes hydrolysis of the triglycerides already stored in the fat cells, insulin inhibits the release of fatty acids into the circulating blood stream, thereby promoting obesity. Insulin also promotes glucose transport through the cell membrane into the fat cells in the same way that it promotes glucose transport into the musde cells. Although some of this glucose is then utilized to synthesize small amounts of fatty acids, the glucose also forms large quantities of glycerophosphate which supplies the glycerol backbone that combines with fatty acids to form triglycerides molecules which are a dominant storage form of fat in adipose cells. Therefore, when insulin is not available, storage of a large amount of fatty acids transported from the liver via lipoproteins is almost totally blocked.

Various studies have investigated the role that insulin plays in weight gain. In the United Kingdom Prospective Diabetes Study (UKPDS), for example, increased weight gain was directly related to improved glycaemic control and intensification of therapy with all pharmacotherapies, (with the exception of the diabetic drug metformin). However, weight gain was greatest in a group treated with insulin, where patients gained on average 6.5 kg. In addition, data from the Diabetes Control and Complication Trial (DCCT) demonstrated that insulin-associated weight gain was significantly greater in patients receiving intensified insulin intervention, compared to conventional intervention.

Fat cells have historically been accredited with two main functions, namely that of storing energy and preserving body temperature via insulation. In the presence of excess intra-abdominal (visceral) fat, however, fat cells, once filled with fat, also assume a hormonal function by manufacturing and releasing various chemical substances called inflammatory cytokines, able to mimic or interfere with normal hormonal functions. For reasons not completely understood, some of these inflammatory cytokines disrupt insulin's role on cellular level (at the insulin receptor that regulates the glucose portal across the cell membrane) and render insulin less effective. The medical term for this condition is 'insulin resistance'. To get the same task done as before, the body compensates by producing even more insulin, and insulin levels rise above the norm.

Because of insulin's obesity-promoting effects, insulin resistance makes one more prone to gaining weight than before. In addition, it also makes it more difficult for one to lose weight. Once this condition sets in, a vicious cycle begins, explaining why many obese individuals, once burdened with excess visceral fat, experience that their metabolism has effectively slowed down.

The invention in this category is based on the proposition that aspects of fat breakdown and use for providing energy are enhanced in the absence of insulin. This can occur normally between meals when secretion of insulin is minimal but the effect becomes extreme in diabetes mellitus when secretion of insulin, is almost absent. When this happens, the aforementioned effects of insulin causing the production and storage of fat, are reversed. A dominant effect is that the enzyme hormone-sensitive lipase in the fat cells becomes strongly activated. This causes hydrolysis of stored triglycerides, releasing large quantities of fatty acids and glycerol from the adipose tissue into the circulating blood. The net effect is significant weight-loss.

A goal in this respect is a strategy in which the insulin level is lowered to a value which is still healthy but which does not promote fat deposition and fat storage, thereby counteracting insulin's obesity-promoting effects.

The invention is inter alia based on the use of a combination of naturally derived compounds and plant extracts that display complementary and synergistic pharmaceutical effects, all of which have been proven to be useful for the treatment or alleviation of insulin resistance. The mode of action is via an unique mechanism, which optimises catabolic metabolism by lowering insulin levels and increasing the usage of fat for energy purposes, thereby assisting with weight loss.

Category C: The Food Environment

Our caveman forefathers used considerable amounts of energy and covered great distances on foot in search of food. Their meals, consisting mainly of low energy-dense foods, were often infrequent and interrupted by regular periods of famine. They also utilized large amounts of energy to maintain their body heat, especially in colder climates and in meagre habitats. In order to survive periods of starvation, the caveman's body perfected ways to store excess energy in the form of body fat. Those with more efficient storage systems had a significant advantage over their less padded friends during periods of famine.

Besides the caveman's body developing more efficient storage systems, the caveman's mind was also gearing for survival, and evolved to prevent weight loss at all costs. This basic instinct comes from the dinosaurs, inherited by cavemen (Homo erectus) and passed along to humans (Homo sapiens). If excess calories are available, appetite promotes weight gain by ensuring that the individual rather eats "too much" than "too little". Matching energy intake and energy expenditure is extremely difficult. A small mismatch of, for example, 1% can lead to the accumulation of 10 000 calories per year, resulting in a weight gain of 1-2 kg per annum.

Modern day man, unlike cavemen, does not experience periods of famine, but still has the same ability to store energy very efficiently. The paradigm has however changed considerably and current lifestyles are vastly different. Food, now significantly more energy-dense for cavemen, has become abundant and many modern lives and social activities revolve around eating. Whilst genetics may permit the problem to occur, the food environment in the form of energy-rich food that is freely available at fast-food restaurants that line our roadways, and the rows of candies at checkout counters drive it.

The worldwide phenomenon of weight gain therefore indicates that the current mechanisms of regulating energy balance are clearly not able to cope with the prevailing obesity-promoting environment. Various mechanisms control appetite and energy intake and much attention has been focused upon the development of anti-obesity drugs that act on the central nervous system and reduce appetite. The withdrawal of numerous central working appetite suppressant drugs, however, such as fenfluramine, rimonabant and sibutramine (in Europe and under consideration in the US), suggest that targeting this pathway is not without problems.

Alternative options are agents that act on the periphery, namely the gastro-intestinal system, to block or prevent calorie absorption. The fat blocker orlistat, marketed under the trade name Xenical and Alli, falls into this category and is currently the only drug registered for the treatment of obesity in Europe.

It is well known that diets high in fat lead to weight gain because of energy overconsumption. This is mainly due to fat's high energy content and low potential for producing satiety. On the other hand, the excess consumption of refined carbohydrates found in sweet snack foods, sodas and desserts is also a major cause for weight gain. Fat, like refined carbohydrates, is rarely eaten in isolation, but more likely in combination. Good examples are French fries and ice cream.

Fat contains more than twice the amount of energy as the same quality of carbohydrate and protein. The human intestine is able to absorb 95% of all dietary fat, and it is therefore not surprising that a high fat diet is readily converted into fatty tissue, especially in individuals with a slow metabolic rate.

In the typical Western diet the dominant source (90%) of fat comes packaged as triglycerides. Each triglyceride consist of three smaller building blocks, called fatty acids, bonded together by a larger carrier molecule called glycerol. Triglyceride molecules are far too large to be absorbed through the intestinal wall, and therefore need to be broken down into smaller particles. This happens during the process of digestion, when fat-digesting enzymes split the bonds between fatty acids and set them free. Once released, each individual fatty acid freely passes through the wall of the small intestine and enters the body.

Fats are medically called 'lipids'. Fat digestion is therefore called 'lipolysis' and the fat-digesting enzymes responsible for this process are the 'lipases". There are several different lipases, released throughout the gastro-intestinal tract. Lipolysis takes place via the combined action of different lipases. The rate at which lipolysis takes place and the consequent supply of free fatty acids to the body can be affected by various factors. These include certain biochemical agents, many of which are naturally occurring or derived from nature.

Like triglycerides, most carbohydrates are too large to be absorbed into the system without the splicing action of digestive enzymes. All carbohydrates are constructed from the elements carbon, hydrogen and oxygen, arranged in a three dimensional ring-like structure. A single ring is called a monosaccharide, two rings are a disaccharide, whilst those with more than two rings are the polysaccharides. For obvious reasons, monosaccharides are the smallest carbohydrate molecules and can be absorbed directly into the body without the need for digestion. Monosaccharides include glucose, the dominant energy molecule of the body, as well as fructose or 'fruit sugar', naturally found in fruit and fruit juice.

The disaccharides include table sugar and milk sugar, whilst the polysaccharides form the various starches. These two groups are the most important source of calories consumed in the average Western diet. Being too large to be absorbed, both disaccharides and polysaccharides require reduction through digestion into smaller molecules like glucose and fructose which can be absorbed and utilised as energy.

Like fat, the digestion of carbohydrate begins in the mouth and continues in the small intestines by the action of various digestive enzymes, mostly produced by the pancreas. This process is completed by another group of enzymes found in the intestines, which include maltase, sucrase, and lactase, collectively known as the aplha-glucosidases.

Nutrients are essential to health and the dominant reason all living creatures must eat a variety of nutritious food. Nutrients enter the body and are absorbed via the intestines. Antinutrients, however, are agents that block or interfere with the absorption of nutrients. Antinutrients are either natural or synthetic compounds and are found at some level in almost all foods for a variety of reasons, including food items that we consume on a daily basis. A common example is phytic acid, found abundantly in sodas and junk food. Phytic acid has the ability to form insoluble complexes with calcium, zinc, iron and copper, thereby reducing their absorption in the intestines and potentially causing a shortage.

Numerous antinutrients are also known to inhibit the action of digestive enzymes, including the lipases and alpha-glucosidases. In this field the inventor based his research and developed a novel unique product which is able to block carbohydrate and fat digestion simultaneously, thereby blocking the absorption of calories from both these sources after consumption.

SUMMARY OF THE INVENTION

Used on its own, each of the three nutritional agents displays a unique weight-loss benefit within its own distinctive category and can effectively be used to treat or prevent obesity as a single or standalone treatment strategy.

The invention is based, however, on the premise that the use of three anti-obesity products, each targeting different obesity promoting mechanisms, will have a synergistic weight loss effect in subjects.

The novel products developed in each individual category will be referred to according to the following schedule: A) behaviour—'MOOD ENHANCER' B) metabolism—'INSULIN SPARING AGENT' and C) the food environment—'PERIPHERAL ENERGY BLOCKER'

DESCRIPTION OF PREFERRED EMBODIMENTS

A—Mood Enhancer

A premise is that the use of a mood enhancer, included in a weight loss program, may be beneficial. It is believed that the effects of a mood enhancer, such as increased endurance and diminished fatigue as well as a heightened sense of emotional and mental wellbeing, would help a subject to be more inclined to begin with, and adhere to, an exercise and diet program.

A mood enhancer, identified as being suitable for use in a weight-loss program, consists of a composition of a plant extract, neutraceutical food extract and two essential minerals, namely inositol, rhodiola rosea, magnesium and zinc, respectively.

Rhodiola rosea is a plant that grows in cold regions around the world. These regions include the Arctic, the mountainous areas of central Asia, the Alps, Scandinavia and Iceland. Traditionally, Rhodiola rosea was used by Siberians and Scandinavians to improve vitality in harsh conditions presented by bitter cold climates and high altitude areas. To improve physical and mental endurance while persevering under stressful conditions, Rhodiola was routinely given to Soviet cosmonauts, KGB secret agents and special force soldiers. Various studies have assessed Rhodiola extract's effect on the neurological function of humans and animals' In particular, studies on human subjects have shown that it improves mood by displaying the rare quality of alleviating both the symptoms of depression and anxiety.

Rhodiola's mode of action appears to be mediated by its influence on the levels of the two most important "happiness" neurotransmitters, namely serotonin and dopamine.

Trials done with Rhodiola extract on patients suffering from mild to moderate depression showed a significant improvement regarding scores of insomnia and emotional instability as compared to placebo.

During another trial, participants with generalized anxiety disorder (GAD) showed a significant improvement in anxiety-related symptoms with Rhodiola extract, as measured via three different psychometric scales, namely the Hamilton Anxiety Rating Scale (HARS), the Four-Dimensional Anxiety and Depression Scale and the Clinical Global Impressions of Severity/Improvement Scale.

Various studies have also demonstrated that Rhodiola rosea extract exerts an anti-fatigue effect that improves general mental performance and increases the ability to concentrate in healthy subjects. One such double-blind, cross-over study, examined this effect in healthy physicians during night duty. During this trial, a statistically significant improvement in perceptive and cognitive cerebral functions was measured in all the doctors that participated in the trail.

Inositol occurs naturally as phytic acid in the fibre component of certain plant foods, and as myo-inositol in meat. Myo-inositol is found to bio-accumulate most abundantly in the central nervous system, where it plays an important role as the structural basis for numerous signalling and secondary messenger molecules. These play a crucial role in a number of biological processes, including nerve guidance, the modulation of serotonin's activity, gene expression and the assembly of the cytoskeleton of neurons.

Studies on inositol supplementation show promising results for people suffering from neuro-psychological conditions such as generalised anxiety disorder, panic disorder, obsessive-compulsive disorder, bulimia, agoraphobia and depression. In a double-blind, controlled trial, inositol proved superior to fluvoxamine, a popular antidepressant belonging to the class of SSRI drugs, (serotonin selective reuptake inhibitors), for decreasing the number of panic attacks.

Research has also indicated that many patients suffering from clinical depression have decreased levels of inositol in their cerebrospinal fluid, the liquid medium that encapsulates the brain. It has been postulated that inositol produces positive clinical results in patients with depression due to the important role that it plays as a messenger molecule for the mood controlling neurotransmitter, 5-HTP (Hydroxytryptamine).

In another double-blind, placebo-controlled study of depressed patients, inositol supplementation resulted in the significant improvement of symptoms Magnesium, in its ionic form, is crucial to the function of all living cells, playing a major role in regulating biological compounds like ATP, DNA and RNA. Over 300 enzymes require the presence of magnesium ions for their catalytic action. Historically, magnesium compounds are commonly used medicinally as laxatives, antacids and, until recently, treatment-resistant depression (TRD).

Magnesium-deficiency is known to lead to the dysfunctional opening of specialised calcium channels (N-methyl-d-aspartate/NMDA coupled), thereby causing neuronal injury and subsequent neurological dysfunction. It is postulated that this pathological development may present in humans with the symptom of depression. Evidence from several studies strongly links magnesium with the intracellular and interneuronal processes associated with certain mood disorders, especially depression.

Studies have also demonstrated the mental benefits of magnesium supplementation. In one animal study, magnesium supplementation was comparable to the anti-depressant drug imipramine. A randomized clinical trial done on humans, however, also showed that magnesium was as effective as imipramine when treating depression.

Zinc stimulates the activity of about 100 different enzymatic reactions in the body and, like magnesium, is an important modulator of glutaminergic transmission in the brain. A growing body of evidence implicates a derangement of zinc homeostasis in the psychopathology as well as treatment of mood disorders.

Zinc's antidepressant-like activity has been examined in a variety of tests and models in laboratory animals as well as human studies. A placebo-controlled, double-blind study of zinc supplementation in imipramine therapy, an antidepressant drug, was conducted in sixty depressed patients fulfilling the DSM-IV criteria for major depression without psychotic symptoms. During this trial zinc supplementation significantly reduced depression scores and facilitated the treatment outcome in antidepressant treatment resistant patients.

B—Insulin Sparing Agent

A premise is that the use of an insulin sparing agent, included in a weight loss program, may be beneficial. It is believed that the effect of lowering insulin levels, via a unique triple action mechanism, is beneficial to weight loss for the reasons mentioned hereinbefore.

The dietary insulin sparing component of the invention is a combination agent indicated for the treatment of insulin resistance, obesity and metabolic syndrome. It contains three biological actives, namely berberine, banaba leaf and inositol.

Berberine is a quaternary ammonium salt from the group of isoquinoline alkaloids found in plants such as Berberis, Hydrastis canadensis and Coptis chinenses. Berberine has demonstrated the property of being able to up-regulate activity on both low-density-lipoprotein receptors (LDLR), as well as insulin receptors (InsR). To explain how this mechanism works, one has to touch on the topic of two common biological processes that happen throughout the body and which, to a large degree, control how the body communicates with cells. These processes are called 'downregulation' and 'upregulation'.

Each cell contains a certain amount of receptors on its surface membrane. The number of receptors can be increased ("upregulate") or decreased ("downregulated"). If a cell has fewer receptors on its surface membrane, it is less sensitive to a chemical messenger that is attempting to communicate with the cell. Examples of chemical messengers are hormones and neurotransmitters. Pharmaceutical drugs, however, or toxins, for that matter, may also occupy these receptors and act as chemical messengers.

An example of downregulation can be illustrated by the insulin receptor sites on the cells of a person with type 2 diabetes. If the number of receptors on the surface membrane decreases, the sensitivity of the membrane to insulin will also decrease. The body will compensate for this by releasing more insulin to complete the same task.

Insulin levels drop by up-regulating activity on insulin receptors (InsR). Studies on berberine demonstrate berberine's ability to stimulate glucose transport across the cell membrane to lower elevated blood glucose levels, to prevent or alleviate insulin resistance, to increase insulin receptor expression and to inhibit adipogenesis in human white preadipocytes.

Banaba (*Lagerstroemia speciosa*) is a medicinal plant that grows naturally in India, Southeast Asia and the Philippines. Tea brewed from the leaves is traditionally used to treat diabetes in Eastern medicine and has been in use for over a century. The hypoglycaemic effect of banaba leaf extract has been shown to be similar to that of insulin. The blood sugar regulating properties of banaba and its ability to increase insulin sensitivity have scientifically been demonstrated in cell culture, animal and human studies. Tighter blood sugar control and a reduction in insulin levels have also demonstrated weight-loss in trials, even in the absence of dietary alterations.

As mentioned, inositol occurs naturally as phytic acid in the fibre component of certain plant foods, and as myo-inositol in meat. It has an important role as a structural basis for numerous signalling and secondary messenger molecules that play a crucial role in a number of biological processes, including insulin signal transduction. Studies in patients with the polycystic ovary syndrome (PCOS), a condition known to be associated with insulin resistance and hyperinsulinemia, have demonstrated that inositol increases the action of insulin by improving insulin sensitivity. As a result, study subjects benefited by showing improved ovulatory function, decreased blood pressure and plasma triglyceride concentrations.

C—Peripheral Energy Blocker

A premise is that the use of a peripheral energy blocker, included in a weight loss program, may be beneficial. It is believed that the effects will assist obese individuals by preventing the digestion of excess fat and refined carbohydrates in their diet, thereby allowing it to pass through their systems without getting absorbed.

In the continual search for novel anti-obesity agents, scientists have screened numerous plant-derived 'phytochemicals' for potential lipase and glucosidase inhibition. One such study examined 132 extracts from 106 plant species, used either as food sources or as medicinal plants, screening them for digestive enzyme inhibition potential. Because of their antinutrient content, the majority of extracts exhibited some degree of digestive enzyme inhibition. Whilst some of these effects were mild, others proved remarkably potent, especially when compared to synthetic drugs. Twenty six extracts, for example, inhibited lipase activity by at least 40%, of which 10 exhibited more than 70% inhibitory activity.

Certain apple extracts inhibited lipase activity by more than 70%. Apples contain several different phenolic substances, which include chlorogenic acid, catechin, phorodzin, rutin and some procyanidins. Other studies have also demonstrated that apple polyphenols display highly effective lipase blocking activity.

Gardeniae fructus is an ancient Chinese medicine used for its painkilling, fever reducing and neuroprotective effects. Its main components are geniposide and crocin. Research has demonstrated that crocin and its metabolite, crocetin, potently inhibit the effect of lipase. In mice fed on a high fat diet, crocetin and crocin significantly reduced fat deposits, and their potency at a dose of 50 mg/kg was found to be comparable with that of orlistat at a dose of 10 mg/kg.

Salacia reticulata is a climber found in Sri Lanka and India. Its roots and stems have been used to treat diabetes for centuries. In Japan, Salacia is consumed as a food supplement for the purposes of suppressing high blood sugar levels. Pharmacological studies have demonstrated that various multi-target actions contribute to Salicia root-extract's improvement of type 2 diabetes, high blood sugar and cholesterol levels, conditions commonly associated with obesity. Scientists have found that Salacia's effects are mainly due to the presence of highly potent glucosidase inhibitors.

The main compounds responsible for a-glucosidase inhibition are salicinol, kotalanol and ponkoranol. In one study, kotalanol demonstrated more potent inhibitory activity against sucrase, the enzyme that digests sucrose (table sugar), than the diabetic drug acarbose. Various studies have shown that the oral administration of a Salacia reticulata extract suppressed body weight gain without affecting food intake. A peripheral energy blocker, containing all the above agents in a proprietary blend, assists obese individuals by preventing the digestion of excess fat and refined carbohydrates. But, besides blocking calorie intake, the peripheral energy blocker has also been designed to assist with appetite control.

Besides the brain, the stomach also plays a role in the regulation of appetite. If one has not had food for a while, the stomach undergoes a series of rhythmic contractions, which present as gnawing, cramp-like sensations in the pit of the stomach. These are commonly referred to as 'hunger pangs'. Once the stomach becomes distended or filled with food, signals from the stomach suppress the feeding centre in the brain, thereby reducing the desire to eat. This mechanism is controlled by nerves which link the stomach with the feeding centre, as well as various chemical messengers, the dominant player being the hormones cholecystokinen and grehlin, released by the intestines when food enters the stomach.

Research has identified a new mechanism called the 'ileal brake' as a novel way to assist with appetite control. Normally, dietary fat is digested and absorbed in the first part of the small intestine, called the duodenum. However, it has long been known that if digestion and absorption of fats take place in the ileum, the second part of the small intestine, a strong feedback signal is activated which slows the gastrointestinal transit time and releases various satiety hormones including cholecystokinen. Thus, the fat digestion in the ileum caused by the peripheral energy blocker applies a 'brake' on the digestive processes by slowing it down, an additional strategy to help reduce calorie intake by reducing appetite.

Table of Preferred Embodiments

TABLE 1

Mood enhancer

| SUBSTANCE | DOSAGE (mg) | DOSAGE RANGE (mg) |
|---|---|---|
| Inositol | 400 | 35-600 |
| Rhodiola rosea | 80 | 5-500 |
| Magnesium | 60 | 5-100 |
| Zinc | 5 | 2-30 |

TABLE 2

Insulin sparing agent

| SUBSTANCE | DOSAGE (mg) | DOSAGE RANGE (mg) |
|---|---|---|
| Berberine | 15 | 5-500 |
| Banaba leaf | 420 | 10-200 |

TABLE 2-continued

Insulin sparing agent

| SUBSTANCE | DOSAGE (mg) | DOSAGE RANGE (mg) |
|---|---|---|
| Inositol | 30 | 5-100 |
| Chromium | 70 mcg | 5-200 mcg |

TABLE 3

Peripheral energy blocker

| SUBSTANCE | DOSAGE (mg) | DOSAGE RANGE (mg) |
|---|---|---|
| Lipase inhibitors | | |
| Gardenia fructus | 250 | 25-500 |
| Apple polyphenols | 150 | 20-550 |
| Glucosidase inhibitors | | |
| Salacia reticulata | 50 | 10-450 |

A daily dosage constitutes between 1-2 tablets of each product between 1-3 times per day.

Trials

A trial was conducted on subjects who were divided into two groups designated Group I and Group II.

Group I was initially administered a placebo and thereafter a supplement of the three products for the remainder of the trial.

Group II was administered a supplement of the three products for the duration of the trial.

The average total weight loss and average weekly weight loss observed for Group II were almost double that of Group I. The cholesterol and glucose content of the blood substantially decreased for Group II, whereas the cholesterol content of Group I had increased and the glucose decrease was significantly less in this group. The average BMI and waist circumference reduction were also significantly more in Group II.

In the final weeks Group I was administered with the supplement.

This was done to rule out genetic differences and environmental circumstances as the cause of the diverse results obtained for the two groups in the first weeks of the trial.

During the final weeks Group I subjects showed a significant increase in average weight loss and BMI and, waist circumference reduction. A substantial decrease in the blood cholesterol content, and blood glucose content in the subjects was also observed during this period.

Similar weight loss and similar BMI and waist circumference reductions were observed for both Groups during the final weeks. Reductions in blood cholesterol and blood glucose content were observed for both Groups.

The observations indicate that the supplements administered to the subjects were a likely cause of the weight reduction and blood cholesterol and blood glucose content reduction that were observed.

The invention claimed is:

1. A pharmaceutical composition for treating obesity in a patient in need thereof consisting essentially of therapeutically effective amounts of:
   (1) rhodiola rosea extract,
   (2) banaba leaf extract, and
   (3) an extract selected from the group consisting of:
   gardenia fructus extract, apple extract, salacia reticulata extract and mixtures thereof.

2. A pharmaceutical composition for treating obesity in a patient in need thereof consisting essentially of a therapeutically effective amount of extracts of rhodiola rosea, banaba leaf, gardenia fructus and salacia reticulata.

3. A composition for treating obesity in a patient in need thereof consisting essentially of therapeutically effective amounts of hydrastis canadensis extract, banaba leaf extract and rhodiola rosea.

4. A composition for treating obesity in a patient in need thereof consisting essentially of therapeutically effective amounts of coptis chinensis extract, banaba leaf extract and rhodiola rosea.

5. A pharmaceutical composition for treating obesity in a patient in need thereof consisting essentially of therapeutically effective amounts of:
   (1) rhodiola rosea extract,
   (2) banaba leaf extract,
   (3) an extract selected from the group consisting of:
   gardenia fructus extract, apple extract, salacia reticulata extract and mixtures thereof, and
   (4) a compound selected from the group consisting of: inositol, magnesium, zinc, berberine and mixtures thereof.

* * * * *